United States Patent [19]

Rakowicz-Szulczynska

[11] Patent Number: 5,100,774

[45] Date of Patent: Mar. 31, 1992

[54] METHODS FOR DETECTING GROWTH FACTOR RECEPTOR EXPRESSION

[75] Inventor: Ewa Rakowicz-Szulczynska, Philadelphia, Pa.

[73] Assignee: The Wistar Institute of Anatomy & Biology, Philadelphia, Pa.

[21] Appl. No.: 185,061

[22] Filed: Apr. 22, 1988

[51] Int. Cl.$^5$ .......................... C07K 3/24; C12Q 1/68; G01N 33/566; G01N 33/574

[52] U.S. Cl. .......................................... 435/6; 435/4; 435/7.23; 435/7.8; 436/63; 436/64; 436/86; 436/501; 436/503; 436/504; 436/538; 436/813; 436/824; 530/412; 530/413; 530/418

[58] Field of Search ................. 436/501, 518, 63, 503, 436/504, 813, 64, 86, 824, 538; 435/7, 4, 7.23, 7.8, 6; 530/412, 413, 418

[56] References Cited

U.S. PATENT DOCUMENTS

| 4,786,593 | 11/1988 | Ross et al. | 436/503 |
| 4,855,241 | 8/1989 | Johnson, Jr. | 436/503 |
| 4,933,294 | 6/1990 | Waterfield et al. | 436/501 |

FOREIGN PATENT DOCUMENTS

| 0179037 | 4/1986 | European Pat. Off. . |
| 0202005 | 11/1986 | European Pat. Off. . |
| WO8200059 | 1/1982 | PCT Int'l Appl. . |

OTHER PUBLICATIONS

H. F. Sears, et al, Cancer Res., 45:5910 (1985).
H. Koprowski, et al, Proc. Nat'l. Acad. Sci., USA, 81:216 (1984).
H. Koprowski, et al, Som. Cell Mol. Genet., 11:297 (1985).
R. N. Fabricant, et al, Proc. Nat'l. Acad. Sci., USA, 74:565 (1977).
G. E. Landreth, et al, Proc. Nat'l. Acad. Sci., USA, 77:4751 (1980).
D. D. Vale, et al, Methods Enzymol, 109:21 (1985).
B. A. Yankner, et al, Proc. Nat'l. Acad. Sci., USA, 76:1269 (1979).
E. M. Rakowicz-Szulczynska, et al, Biochem. Biophys. Res. Comm., 140:174 (1986).
E. M. Rakowicz-Szulczynska, et al, Proc. Nat'l. Acad. Sci., USA, 83:3728 (1986).
L. K. Johnson, et al, Nature, 287:340 (1980).
U. Y. Yeh, et al, Proc. Nat'l. Acad. Sci., USA, 84:2317 (1987).
M. B. Omary, et al, Science, 238:1578 (1987).
M. Keating and L. T. Williams, Science, 239:914-916 (1988).
C. Ernst, et al, Amer. J. Pathol., 117:451 (1984).
M. Herlyn, et al, J. Immunol., 134:4226 (1985).
U. Rodeck, et al, Cancer Res., 47:3692 (1987).
M. B. Sporn and A. B. Roberts, Nature, 332:217-219 (1988).
Buller et al, "Progesterone-binding Components of Chick Oviduct", Journal of Biological Chemistry 250:809-818.
Rohrer et al, "Internalization of Nerve Growth Factor . . . ", Journal of Neuroscience, 2:68-697 (1982).
Loosfelt et al, "The Rabbit Progesterone Receptor", J. of Biological Chemistry 259:14196-14202 (1984).
Chard, T., *An Introduction to Radio immunoassay and Related Techniques*, Amsterdam, Netherlands (1978), pp. 456-457.
Matsuzawa, A. et al, 1987, Comparative Studies of Estrogen Receptors Between A Pregnancy-dependent Mouse Mammary Tumor . . . Endocrinol. 120, 2346.
Matsuzawa, A. et al, 1983, Differential Response of An Ovarian Responsive Tumor to Androgenic & Estrogenic . . . Can. Res. 43, 3680.
Rakowicz-Szulczynska, 1986, Chromatin Binding of Epidermal Growth Factor, Nerve Growth Factor and PDGF . . . PNAS 83, 3728.
Rakowicz-Szulczynska, 1986, Identification of NGF Receptor in Chromatin of Melonoma Cells using Monoclonal . . . BBRC 140, 174.
Odell, W., 1983, Separation of Bound from Free Hormone, In: Principles of Competative Protein-Binding Assay, John Wiley & Sons, New York.

*Primary Examiner*—David Saunders
*Attorney, Agent, or Firm*—Howson and Howson

[57] ABSTRACT

Methods are provided for the detection of the synthesis of growth factor receptors or cell surface antigens by tumor cells, and for the isolation thereof.

9 Claims, No Drawings

METHODS FOR DETECTING GROWTH FACTOR RECEPTOR EXPRESSION This invention relates generally to the detection of growth requirements of certain tumor cells. More specifically, the invention relates to the detection of growth factor cell surface receptors expressed at very low levels on tumor cells. The research which resulted in the present invention was supported by grants from The National Institutes of Health.

BACKGROUND OF THE INVENTION

Detection of cell surface antigens, particularly growth factor receptors, expressed at elevated levels by tumor cells as compared with normal cells is of particular concern in the fields of immunodiagnosis and immunotherapy of human tumors. See, e.g., H. F. Sears, et al, *Cancer Res.*, 45:5910 (1985); H. Koprowski et al, *Som. Cell Mol. Genet.*, 11:297 (1985); and H. Koprowski et al *Proc. Nat'l. Acad. Sci., USA,* 81:216 (1984). Efficient methods of detection of growth factor receptors would allow the determination of the growth requirements of tumor cell types and thus enable the development of therapeutic methods for reducing the growth and limiting the spread of such tumor cells in patients having certain cancers.

Presently three methods are primarily used to determine if a tumor cell or tumor cell line is expressing or over-expressing a particular receptor for a specific growth factor. One current approach to testing receptor expression is based on the analysis by radioimmunoassay ("RIA") of growth factor binding to the cell surface using intact cells. Such an assay is described in R. N. Fabricant et al, *Proc. Nat'l. Acad. Sci., USA,* 74:565 (1977); G. E. Landreth et al, *Proc. Nat'l. Acad. Sci., USA,* 77:4751 (1980); and D. D. Vale et al, *Methods Enzymol,* 109:21 (1985). However, such RIAs are frequently performed at 0 C to inhibit internalization of growth factor molecules. These methods are not particularly sensitive, lacking qualitative accuracy and frequently providing false negative results. A number of recent studies have indicated that the uptake and nuclear accumulation of growth factors in assays performed at 0° C. do not reflect the dynamic aspects of growth factor binding under physiological conditions. Moreover, some surface receptors may be synthesized at levels below the detection limits of the assay. However, even at low levels such receptors may effectively transport growth factors into the cell and thus encourage the growth and multiplication of that particular tumor cell. See, e.g., B. A. Yanker et al, *Proc. Nat'l. Acad. Sci., USA,* 76:1269 (1979); E. M. Rakowicz-Szulczynska et al, *Biochem. Biophys. Res. Comm.,* 140:174 (1986); E. M. Rakowicz-Szulczynska et al, *Proc. Nat'l. Acad. Sci., USA,* 83:3728 (1986); L. K. Johnson et al, *Nature,* 287:340 (1980); U. Y. Yeh et al, *Proc. Nat'l. Acad. Sci., USA,* 84:2317 (1987); M. B. Omary et al, *Science,* 238:1578 (1987).

Additionally such methods detect only those receptors expressed on the cell surface, and cannot detect receptors which are synthesized intracellularly and not expressed on the cell surface. Certain tumor cells synthesize both a receptor and an appropriate growth factor. Expression of the receptor on the cell surface may be undetectable because of a constant down regulation of the receptor by interaction with the synthesized growth factor in the cytoplasm. For example, some melanoma and colorectal carcinoma cells express platelet derived growth factor ("PDGF"), which is critical for their growth, but assays for the PDGF receptor fail to detect receptor on the cell surface. M. Keating and L. T. Williams, *Science* 239:914–916 (1988), reported that this result was due to an autocrine stimulation of v-sis oncogene-transformed cells. This involves an intracytoplasmic interaction of v-sis product with PDGF receptor and consequently results in an undetectable level of PDGF receptor expression on the cell surface. For these reasons, the RIA detection of growth factor binding to intact cells is a less than desirable methodology.

Another commonly used method for determining the presence and identity of growth factor receptors on tumor cells involves the use of monoclonal antibodies developed to these receptors. Binding of monoclonal antibodies to the cell surface is usually analyzed by immunoperoxidase staining, such as described by C. Ernst et al, *Amer. J. Pathol.,* 117:451 (1984), the mixed hemadsorption assay described by M. Herlyn et al, *J. Immunol.,* 134:4226 (1985), or by RIA as described by U. Rodeck et al, *Cancer Res.,* 47:3692 (1987). This method however is very expensive and requires for its performance a monoclonal antibody capable of identifying the cell surface receptor with the appropriate specificity and binding affinity. Without the prior provision of such a monoclonal antibody, this method cannot be used.

Additionally, this method, while very sensitive, also restricts the analyses to the cell surface receptors. Thus, a negative result obtained in this method also does not eliminate the possibility of the intracellular interaction of a synthesized receptor in the cytoplasm with simultaneously synthesized growth factor by the same cell.

Finally, a third method conventionally employed to detect expression of growth factor receptors is the Northern blot analysis, which detects specific receptor mRNA. While this method is very sensitive it also requires the availability of specific DNA probes derived only for those growth factor receptor genes that are cloned and sequenced. Thus in the absence of the cloned receptor gene, this method does not provide an appropriate tool to detect receptors on tumor cells.

Methods for detecting and determining the nutritional requirements of tumor cells for certain growth factors enable the analysis of which growth factors may be selectively used for therapeutic applications, as described in M. B. Sporn and A. B. Roberts, *Nature,* 332:217-219 (1988).

There exists, therefore, a need in the art for additional methods of detecting and quantitating expression of growth factor receptors by tumor cells.

SUMMARY OF THE INVENTION

The present invention provides novel methods for determining the presence and quantity of growth factor receptors synthesized by selected tumor cell lines for use in evaluating and designing therapeutic agents to destroy or inhibit the growth of these tumors.

Method I is based on the precipitation of an insoluble complex formed after binding of the selected growth factor to the appropriate intracytoplasmic receptor bound to the polysome. This precipitate forms after incubation of membrane-free cytoplasm from a selected tumor cell with a selected growth factor if the receptor for that growth factor is expressed by the tumor cell. The precipitate contains growth factor, receptor and an appropriate mRNA synthesized in the cytoplasm.

In Method II, the presence of a receptor is determined by measurement of the nuclear transport of a selected labelled growth factor, which is specifically inhibited in the presence of receptor actively synthesizing in the cytoplasm.

These methods of the invention are much more sensitive than existing approaches and unexpectedly permit the detection and analysis of intracytoplasmic receptor, even in the absence of expression on the cell surface. Additionally, these methods do not require monoclonal antibodies (MAbs) or DNA probes. However, Method I and, in some cases, Method II can also be adapted for the rapid detection of surface antigen expression using MAbs.

These methods may be used for research purposes, i.e. to determine which cell lines express which growth factor receptors or to determine the growth requirements of certain tumor cell lines. The methods may be employed in selecting an appropriate therapeutic agent for use against a specific tumor.

The methods of the present invention also allow the isolation and characterization of unknown cell surface receptors from tumor cell lines by purifying receptor from the precipitate of Method I. The mRNA of the receptor is present in the precipitate and may be further purified and analyzed. Thus these methods may allow the determination of the factors that bind to such receptors and are transported into the tumor cell. This further identification and analysis of the structure of certain growth factor receptors may also aid in the selection and/or design of therapeutics, e.g., monoclonal antibodies and synthetic drugs capable of binding to these receptors.

In the examples below, the methods of the invention were used to identify nerve growth factor ("NGF") and epidermal growth factor ("EGF") receptor expression on cell lines described previously as receptor-negative. PDGF receptor was identified in tumor cell lines which produce PDGF but did not show the receptor expression in PDGF-surface binding studies and Northern blot analyses of RNA.

Other aspects and advantages of the present invention are disclosed in the following detailed description of presently preferred embodiments.

DETAILED DESCRIPTION OF THE INVENTION

The first method of this invention ("Method I") involves the precipitation of actively synthesized receptor with polyribosomal mRNA of a selected growth factor. Pure membrane-free cytoplasm from a selected tumor cell or cell line is incubated with an excess of a selected growth factor at room temperature.

In cytoplasm containing actively synthesized receptor for the selected growth factor, a precipitate will form at physiological conditions. The precipitate consists of a complex of synthesizing receptor, polysomal mRNA and the selected growth factor.

For performance of this method, pure membrane free cytoplasm may be prepared by conventional methods, desirably from between 5 to $20 \times 10^6$ tumor cells. The cytoplasm from these tumor cells is incubated for about 10 minutes at room temperature with desirably between about 100 nanograms to about 2 micrograms of the growth factor. Physiological conditions for this incubation include pH 7.0 and a low concentration of receptor, or growth factor. Observation of the formation of a precipitate indicates the presence of the receptor for the selected growth factor in that tumor cell line. The time required for formation of the precipitate in this room temperature incubation will depend upon the amount of receptor synthesized by the cell and the amount of growth factor employed. Generally a time sufficient for the precipitate to form is less than 1 hour, and can be as short as about 10 minutes.

To permit quantitation of the growth factor receptor, the precipitate may further be centrifuged from the cytoplasm-growth factor mixture, quantitated and removed therefrom. To ensure the most accurate quantitation, prior to centrifugation the cytoplasm containing the precipitate may desirably be incubated a second time at 0° C., for about 2 hours. This second incubation at the lower temperature maximizes the amount of precipitate to be centrifuged, and also decreases the effects of degradation of the precipitate.

The receptor may then be purified from the centrifuged precipitate and subjected to conventional techniques to determine its structure and sequence. The precipitate mRNA may be further purified and used for cloning and sequencing, or translation in vitro. The total amount of time to perform Method I is between about 4 to 6 hours.

In Method I, the growth factor may optionally be conventionally labelled, e.g. with $^{125}$I or any other label conventionally employed for detection of biological substances. Alternatively, the cytoplasmic RNA may be labeled e.g., with $^3$H-uridine. Selection and use of an appropriate label is considered to be well within the realm of one of skill in the art and does not impose any limitations on the present invention.

In a practical application, e.g., for rapid screening of growth factor receptor synthesis in a biopsy of a tumor cell, the amount of a labeled growth factor employed in the method and present in the precipitate may also be analyzed. Once a particular precipitate is removed, the remaining cytoplasm is free to be assayed with another growth factor and the steps continued. In this way Method I allows one to distinguish those tumor cells which express a receptor for a specific growth factor from those tumor cells which do not synthesize that receptor. Additionally, cross-reactivity of different growth factors with the analyzed receptor may be assayed.

This method of the invention may also be used with monoclonal antibodies directed against the receptors, as well as growth factors. Monoclonal antibodies developed against tumor antigens of unknown structure and function employed in this method may allow identification of those antigens. This test is especially helpful if the MAb recognizes a surface antigen for which the appropriate cDNA or gene has not been cloned, and probes are not available.

A second method provided by the invention ("Method II") also involves the detection of receptors for a specific growth factor. This method is based on competitive inhibition of the nuclear transport of a selected labeled growth factor in a cell-free system in the presence of actively synthesizing receptor which binds the growth factor. Method II, because of its sensitivity, may be used alone or in addition to Method I, if the results of Method I are negative.

Method II involves incubating isolated nuclei of a selected tumor cell with a selected labeled growth factor at different concentrations at room temperature in several different fractions: crude tested cytoplasm, pure membrane-free cytoplasm, synthetic medium, and synthetic medium plus a microsomal fraction from a tumor cell line. This sensitive method may be desirably conducted employing about 0.10-20 nanograms of labeled growth factor per milliliter, cytoplasm from $4-5 \times 10^6$ tumor cells and $3-4 \times 10^6$ nuclei. The isolated nuclei of control or tumor cells are incubated with labeled growth factor at different concentrations for about one hour in a selected fraction. If the fraction tested by this method contains actively synthesized receptor, inhibition of nuclear uptake of growth factor is observed because of competition between the nuclei and the synthesizing receptor present for the available growth factor. Inhibition results from the formation of a precipitate of complexes of polysome-bound receptor, mRNA and labelled growth factor outside of the nuclei, if receptor for the selected growth factor is present in the fraction. In cells that do not express the receptor, an inhibition of the nuclear transport of growth factor is not observed because no extranuclear precipitation occurs. Thus, inhibition of nuclear transport in a pure membrane-free cytoplasm compared to the synthetic medium is a sufficient comparison to show that the receptor is being synthesized by the tumor cells.

Generally, in the presence of synthesizing receptor for the selected growth factor, inhibition of nuclear transport is observed in all fractions but synthetic medium. Where receptor is expressed at very low levels by the tested cells, inhibition may only be observed in one or two of these fractions.

Quantitation of inhibition involves measuring the amounts of $^{125}$I-labelled growth factor taken up by isolated nuclei of tumor cells, in the presence of cytoplasm compared to the amount of labeled growth factor taken up by nuclei in synthetic medium. Method II can be conducted rapidly, in about 4 hours.

The methods of this invention thus enable the selection of therapeutic agents directed against overexpressed receptor on selected tumor cells, or receptor expressed at low levels and intracytoplasmically that are identified by these methods. The methods of the invention may be employed to examine biopsied tumor cells to identify receptors against which an applicable therapy should be addressed. The application of these methods in cancer diagnosis would thus aid in selecting an agent for the destruction of such cells in vivo. For example, the identification of which receptor is overexpressed on a particular tumor cell line or expressed in low levels in the cytoplasm could indicate which monoclonal antibody would be most appropriate for treatment and possible destruction of the tumor. Likewise, if synthetic compounds exist which are capable of binding to a receptor identified by the methods of this invention, the selection of such binding compounds may also be indicated by performance of the methods of the invention. The selection of such a binding agent which competitively binds to the receptor could deprive the tumor cell of the growth factor it needs to proliferate.

Certain growth factors are multi-functional, activating the proliferation of some cells, but inhibiting the proliferation of others. Identification of the intracellular receptors, not expressed on the cell surface, thus not recognized by anti-tumor cell drugs acting on the cell surface opens new avenues for determining which compounds may be taken up by the cell, selectively binding intracytoplasmic receptors. Thus, specific inhibiting growth factors may be selected for therapeutic application by use of the present methods.

The following examples are provided to illustrate embodiments of the invention, however the invention is not limited to only the illustrated embodiments. In the examples below model experiments are described using NGF, PDGF, EGF and MAb ME491. The methods are also effective in detecting insulin, IGF-I and other growth factor receptor expression.

EXAMPLE 1—METHOD I—PRECIPITATION OF SYNTHESIZED RECEPTOR

The known available tumor cell lines employed in Method I in this example are: A875, HS294 and WM9 melanoma cells; and SW948, SW707 and SW1116 colorectal carcinoma cells. Cells grown as monolayers were incubated for 18 hours with $^3$H-uridine (20 $\mu$Ci/ml, specific activity, 46 Ci/mmol), or $^{35}$S-methionine (30 $\mu$Ci/ml, specific activity, 1000 Ci/mmol) and $^{35}$S-cysteine (30 $\mu$Ci/ml, specific activity, 800 Ci/mmol). After incubation, cells were washed 5 times with ice-cold PBS and briefly homogenized in 20 mM Tris-HCl, pH 7.6, 1 mM EDTA, (5 ml/20 $\times 10^6$ cells) and centrifuged at $800 \times g$ for 10 minutes. The supernatant was defined as the crude cytoplasm which after centrifugation ($105,000 \times g$ for 60 minutes) yielded membrane-free cytoplasm and a pellet of the microsomal fraction. See e.g. RakowiczSzulczynska et al, *Proc. Natl. Acad. Sci. USA.* 83, supra.

Membrane-free cytoplasm isolated from $20 \times 10^6$ cells (3-5 ml) was incubated with 0.5-2 $\mu$g of unlabeled or $^{125}$I-labeled NGF, PDGF, EGF or MAb ME 491 dissolved in 200 $\mu$l of PBS at room temperature for 10 minutes, and further incubated for 2 hours at 0° C. In some experiments, the mixture was frozen overnight at $-20°$ C., or for 10 minutes at $-70°$ C. The precipitate formed was collected by centrifugation at 110 000 $\times$ g for 60 minutes.

The precipitate was divided into two parts. The first part was dissolved in 50 $\mu$l of 0.1M Tris-HCl, pH 7.9, 2% SDS, 1% 2-mercaptoethanol, 0.2M NaCl and electrophoretically analyzed by SDS-PAGE according to Laemmli, *Nature,* 227:680 (1971). The second part was dissolved in 100 $\mu$l of 50 mM Tris-HCl, pH 7.9, 20 mM EDTA, 0.3 m NaCl, 2% SDS and incubated for 1 hour with proteinase K (100 $\mu$g/ml), treated with phenol-chloroform (1:1) and precipitated with 2 parts ethanol. The RNA precipitate was electrophoretically separated in 1.1% agarose gel containing 2.2 M formaldehyde, transferred to nitrocellulose filters and analyzed by Northern blot hybridization with a full-length cDNA probe for the NGF receptor gene cloned in a Sp6 vector [described in Johnson et al, *Cell,* 47:545 (1986) and kindly provided by M. Chao, Cornell University Medical College] labeled with [$\alpha$-$^{32}$P]TTP by nick-translation to specific activity $3 \times 10^8$ cpm/$\mu$g.

After autoradiographic exposure, filters were washed for one hour with boiling water and rehybridized to [$\alpha$-$^{32}$P]TTP-labeled pSA082 containing cDNA for human $\alpha$-enolase. pSA082 is described in A. Giallongo et al, *Proc. Nat'l. Acad. Sci., USA,* 83:6741 (1986) and was kindly provided by L. Showe (The Wistar Institute). Probe labeling and Northern blot hybridization was performed according to T. Maniatis et al "Molecular Cloning, A Laboratory Manual", Cold Spring Harbor Laboratory, Cold Spring Harbor, NY (1982).

A. Precipitation of the NGF receptor by Method I

Results of detection of NGF receptor by conventional RIA and by Method I as described herein are shown in Table I below.

In Method I, NGF (Sigma) incubated with membrane-free cytoplasm of cells that express the receptor formed a readily observed precipitate which was absent in cytoplasm of SW948 cells that did not express the receptor. Two cell lines (SW1116 and WM 266-4) which by RIA do not express cell surface NGF receptor also showed positive reaction in Method I. The precipitate collected from cytoplasm labeled with $^3$H-uridine showed high incorporation, as did the precipitate from $^{35}$S-methionine plus $^{35}$S-cysteine-labeled cytoplasm, indicating the presence of both protein and RNA in the precipitate.

RNA and protein components of the precipitate were analyzed in A875 melanoma cells. Northern blot hybridization of the RNA isolated from the precipitate with a [$^{32}$P]TTP-labeled cDNA probe of the NGF receptor gene revealed 3.5 kilobase pair (kbp) bands in both the precipitate and in control RNA of cells expressing the NGF receptor. The α-enolase cDNA probe hybridized only to the control RNA.

To analyze the protein component of the precipitate, cytoplasm was incubated with $^{125}$I-labeled NGF and the precipitate analyzed by SDS-PAGE. A 78 kilodalton (kd) band labeled with $^{125}$I-NGF was detected, containing the NGF surface receptor (65 kd)-NGF monomer complex (13 kd). When the cross-linking agent (dimethyl superimidate) was present during precipitation, in addition to 78 kd band, a 175 kd band was observed which corresponds to the dimer of NGF receptor and the dimer of NGF. Thus NGF mixed with membrane-free cytoplasm specifically precipitates the synthesizing NGF receptor and its polysomal mRNA.

TABLE I

Detection of NFG receptor expression by conventional cell surface test and NGF precipitation of cytoplasm (Method I)

| Cell line | Surface receptor expression in radio-immunoassay | Method I Precipitate formation |
|---|---|---|
| HS294 | + + + + | + + + |
| A875 | + + + | + + + |
| WM9 | + | + + |
| SW707 | + | + + |
| SW1116 | undetectable | + |
| WM266-4 | undetectable | + |
| SW948 | undetectable | − |

B. Precipitation of PDGF receptor from cells which express and do not express the receptor on the cell surface Cytoplasm from melanoma cell lines WM 266-4 and colorectal carcinoma SW 707 which do not express cell surface PDGF receptor and show negative Northern blot hybridization with a probe of PDGF receptor cDNA was incubated with $^{125}$I-PDGF. A precipitate formed which, analysed by SDS-PAGE electrophoresis, showed a band of 180 kd. mRNA isolated from the precipitate was translated in vitro, showing a synthesis of a protein of 165 kd.

Thus it appears that PDGF (15 kd monomer) (Collaborative Research) binds to synthesizing PDGF receptor, precipitating a polysomal complex containing mRNA and PDGF receptor. Since previously Northern analyses of total polyA RNA from SW 707 cells and WM 266-4 cells did not show hybridization with the cDNA probe of PDGF receptor, the isolated RNA may represent a message for the unknown PDGF receptor recognized by alpha-PDGF secreted by the tested cells. Table II below reports the comparison of detection by radioimmunoassay and detection by Method I.

TABLE II

Detection of PDGF receptor expression by conventional cell surface test and PDGF precipitation of cytoplasm (Method 1) (Example 1B)

| Cell line | Surface receptor expression in radio-immunoassay | Method I Precipitate formation |
|---|---|---|
| WI 38 | + + | + + |
| WM 266-4 | undetectable | + |
| SW 707 | undetectable | + |

C. Precipitation of the EGF receptor from cells which express and do not express detectable levels of receptor on the cell surface Cytoplasm from A 431 epidermoid carcinoma cells that express high level of cell surface receptor, from SW 948 colorectal carcinoma that express EGF receptor in lower quantities than A 431 cells, and from SW 707 cells which do not express cell surface EGF receptor were incubated with EGF (Amgen). A precipitate was formed in all cell lines tested, although the amount of the precipitate in SW 707 cells was much lower than in A 431 and SW 948 cells. Thus the receptor in SW 707 cells is expressed, although the level of expression is undetectable by conventional cell surface RIA. See results reported in Table III below.

TABLE III

Detection of EGF receptor expression by conventional cell surface test and EGF precipitation of cytoplasm (Method 1) (Example 1C)

| Cell line | Surface receptor expression in radio-immunoassay | Method I Precipitate formation |
|---|---|---|
| A 431 | + + + | + + + |
| SW 948 | + + | + + |
| SW 707 | undetectable | + |

EXAMPLE 2—APPLICATION OF METHOD I FOR ANALYSIS OF SURFACE ANTIGEN EXPRESSION USING MAbs

MAb ME 491, directed against a surface antigen of unknown function [A. H. Ross et al, Proc. Nat'l. Acad. Sci. USA, 81:6685 (1984)], was used to analyze ME491 antigen expression in WM9 melanoma and SW948 colorectal carcinoma cells known to express ME491 antigen (Atkinson et al, supra; Ernst et al, supra). Incubation of pure membrane-free cytoplasm from both cell lines with MAb ME 491 resulted in formation of a specific precipitate, which in Northern blot analysis, specifically hybridized with the $^{32}$P-labeled cDNA probe of the ME491 gene but not with the α-enolase cDNA control probe. The precipitate portion represents the ME491 antigen.

EXAMPLE 3—METHOD II—NUCLEAR TRANSPORT INHIBITION

If the precipitate of Example 1 is obtained in amounts insufficient for clear interpretation, Method II can be used. In this method of the invention four assays are performed simultaneously. Nuclei were isolated by cell homogenization in 0.25M sucrose, 10 mM KCl, 1.5 mM $MgCl_2$, 100 mM Tris-HCl, pH 7.6, 12 mM 2-mercaptoethanol, 0.02% Triton X-100 (7 ml/10×$10^6$ cells) and centrifugation at 600×g for 10 minutes, followed by ultracentrifugation through 5 ml of 2.2M sucrose, 10 mM Tris-HCl, pH 7.9, 1.5 mM $MgCl_2$ (90,000×g for 60 minutes).

Isolated nuclei were resuspended in i) crude cytoplasm, 2) purified membrane-free cytoplasm, 3) synthetic medium [0.25M sucrose, 20 mM Tris-HCl, pH 7.8, 10 mM $MgCl_2$, 500 ng/ml bovine serum albumin (BSA)], and 4)/synthetic medium mixed with isolated microsomal fraction, and incubated with $^{125}$I-NGF (10 ng/ml) for 1 or 2 hours at room temperature or 37° C. In each assay, 2–3×$10^6$ nuclei per ml was incubated in the cytoplasm prepared from 4×$10^6$ cells.

After incubation, nuclei were centrifuged (600×g for 10 minutes), washed with 50 mM Tris-HCl, pH 7.5, 12.5 mM NaCl, 12.5 mM $MgCl_2$, homogenized in 1 mM PMSF, 1 mM Tris-HCl, pH 7.6 and centrifuged through 1.7M sucrose, 10 mM Tris-HCl, pH 7.9. Nucleoplasm, nuclear membranes and chromatin were separated as described above. Radioactivity bound to particular nuclear fractions was measured. When total nuclear uptake was measured, nuclei were washed and centrifuged through 2.2M sucrose, 10 mM Tris-HCl, pH 7.9, 1.5 mM $MgCl_2$ (90,000×g for 60 minutes) after the incubation.

$^{125}$I-NGF and nuclei were incubated in synthetic medium, where the amount of growth factor taken up by nuclei represents 100% (assay 1). Labelled growth factor and nuclei were also incubated in membrane-free cytoplasm (assay 2). Inhibition is observed in assay 2 if the growth factor receptor is synthesized, and nuclear transport is activated in cells that do not express the receptor. Positive results in assay 2 (inhibition of the nuclear transport observed in assay 1) are sufficient to conclude that the receptor is synthesized. Negative results in assay 2 (no inhibition compared with results in assay 1) might reflect synthesis at levels too low to competitively inhibit NGF transport.

Assays in crude, membrane-containing cytoplasm (assay 3) and in synthetic medium mixed with the microsomal fraction (assay 4) were also performed. Negative results in assays 3 and 4 confirm assay 2 and suggest that the receptor is not synthesized.

Table IV illustrates the results obtained using Method II. The efficient uptake of NGF by isolated nuclei in synthetic medium (assay 1) was competitively inhibited in the presence of cytoplasmic fractions derived from cells expressing the receptor (melanoma cells HS294 and A875), whereas no inhibition was observed using cytoplasmic fractions from cells not expressing the receptor (colorectal carcinoma cells SW948). In A875 and HS 294 melanoma cells, the membrane-free cytoplasm (assay 2) inhibited nuclear uptake to 45 and 36%, respectively, suggesting that the receptor is synthesized. In A875 cells in the presence of crude cytoplasm (assay 3), nuclear uptake is inhibited to 10%. Addition of the microsomal fraction to the synthetic medium (assay 4) reduced nuclear uptake to 77%.

In HS294 cells in the presence of crude cytoplasm, nuclear uptake was only slightly lower than in pure cytoplasm. Similarly, addition of the microsomal fraction to the synthetic medium reduced nuclear uptake only to 96%.

SW948 colorectal carcinoma cells were negative in assays 2, 3 and 4, consistent with both surface binding studies and the negative results in Method I of Example 1 (Table I).

TABLE IV

Nuclear transport of $^{125}$I-NGF in synthetic medium (1), pure, membrane-free cytosol (2), crude cytoplasm (3) and synthetic medium mixed with microsomal fractions (4)

| Cell line | Medium | Molecules/nucleus | % |
|---|---|---|---|
| A875 | 1 | 8,900 | 100 |
|  | 2 | 3,250 | 36 |
|  | 3 | 900 | 10 |
|  | 4 | 6,900 | 77 |
| HS294 | 1 | 41,300 | 100 |
|  | 2 | 18,600 | 45 |
|  | 3 | 17,200 | 42 |
|  | 4 | 39,720 | 96 |
| SW948 | 1 | 13,570 | 100 |
|  | 2 | 22,350 | 164 |
|  | 3 | 22,930 | 169 |
|  | 4 | 13,550 | 100 |

The methods of the invention not only increase the sensitivity of receptor detection, but also provide techniques for the rapid identification of both the receptor and appropriate mRNA.

Numerous modifications and variations of the methods of this invention are expected to occur to those of skill in the art. For example, the methods described above for use with NGF, EGF and PDGF, may also be employed with a variety of growth factors and monoclonal antibodies. Any tumor cell may be so assayed for its growth factor requirements based on the presence and level of expression of growth factor receptor. Thus, the invention and such modifications are encompassed by the appended claims.

What is claimed is:

1. A method for rapid detection of intracytoplasmic synthesis by a tumor cell of a receptor for a selected growth factor protein comprising incubating at room temperature membrane free cytoplasm from said tumor cell and an excess of a selected growth factor for less than one hour and detecting by observation of the cytoplasm-growth factor mixture the formation of a precipitate comprising a complex of synthesizing receptor, polysomal mRNA, and the selected growth factor, the presence of precipitate indicating that said cell contains actively synthesizing receptor capable of binding to said selected growth factor.

2. The method according to claim 1 further comprising quantifying said receptor synthesis by centrifuging said precipitate from the cytoplasm-growth factor mixture and measuring the amount of precipitate to determine the level of growth factor binding.

3. The method according to claim 2 further comprising prior to said centrifugation incubating the product of the room temperature incubation at 0° C. for about two hours to ensure maximal precipitate formation and to decrease degradation of said precipitate.

4. The method according to claim 3 further comprising removing said precipitate and repeating said incubation steps with a second selected growth factor.

5. The method according to claim 1 wherein said growth factor is labelled.

6. The method according to claim 1 wherein said cytoplasm is labelled.

7. A method for detecting and quantifying low level expression by a tumor cell of a receptor for a selected growth factor comprising:
   a. incubating separately at room temperature isolated nuclei of a selected tumor cell with different concentrations of the selected labelled growth factor (i) in synthetic medium, (ii) in pure-membrane free cytoplasm of said tumor cell, (iii) in cytoplasm of said tumor cell containing cell membrane and, (iv) in synthetic medium containing microsomal fractions from said tumor cell for a time sufficient to permit said nuclei to incorporate said labelled factor; and
   b. measuring and comparing the levels of nuclear uptake of said growth factor in each of (i), (ii), (iii) and (iv), wherein if receptor capable of binding said factor is synthesized by said tumor cell nuclear uptake of the factor is inhibited by formation of a precipitate of complexes of polysomal mRNA, synthesizing receptor and growth factor in at least one of ii, iii, or iv.

8. A method for rapid detection of intracytoplasmic synthesis by a tumor cell of a receptor for a selected growth factor protein comprising incubating at room temperature membrane free cytoplasm from said tumor cell and an excess of an antibody to a selected growth factor receptor for less than one hour and detecting by observation of the cytoplasm-antibody mixture the formation of a precipitate comprising a complex of synthesizing receptor, polysomal mRNA and the antibody, the presence of precipitate indicating that said cell contains actively synthesizing receptor capable of binding to said antibody.

9. A method for determining the structure and sequence of a growth factor receptor and the corresponding mRNA comprising the steps of
   incubating at room temperature membrane free cytoplasm from said tumor cell and an excess of a growth factor for less than one hour and detecting by observation of the cytoplasm-antibody mixture the formation of a precipitate comprising a complex of synthesizing receptor, polysomal mRNA and said growth factor, the presence of precipitate indicating that said cell contains actively synthesizing receptor capable of binding to said selected growth factor;
   incubating the product of the room temperature incubation at 0° to ensure maximal precipitation and to decrease degradation;
   centrifuging said precipitate from the cytoplasm-growth factor mixture;
   purifying said receptor and said mRNA from said precipitate separately;
   determining the structure and sequence of the purified receptor; and
   determining the structure and sequence of the purified mRNA.

* * * * *